United States Patent
May et al.

(10) Patent No.: US 9,194,009 B2
(45) Date of Patent: Nov. 24, 2015

(54) MUTANTS FOR THE PREPARATION OF D-AMINO ACIDS

(75) Inventors: Oliver May, Frankfurt (DE); Stefan Buchholz, Hanau (DE); Michael Schwarm, Alzenau (DE); Karlheinz Drauz, Freigericht (DE); Robert J. Turner, Aurora, IL (US); Ian Fotheringham, Lothian (GB)

(73) Assignee: EVONIK DEGUSSA GmbH, Essen (DE)

( * ) Notice: Subject to any disclaimer, the term of this patent is extended or adjusted under 35 U.S.C. 154(b) by 896 days.

(21) Appl. No.: 12/357,218

(22) Filed: Jan. 21, 2009

(65) Prior Publication Data

US 2009/0203091 A1 Aug. 13, 2009

Related U.S. Application Data

(63) Continuation of application No. 10/527,061, filed as application No. PCT/EP03/11432 on Oct. 15, 2003, now abandoned.

(30) Foreign Application Priority Data

Nov. 4, 2002 (DE) .................................. 102 51 184

(51) Int. Cl.
*C12P 13/04* (2006.01)
*C12N 15/09* (2006.01)
*C12N 9/90* (2006.01)
*C12N 1/00* (2006.01)
*C12R 1/19* (2006.01)
C12P 41/00 (2006.01)
C12N 9/86 (2006.01)
C12N 9/06 (2006.01)

(52) U.S. Cl.
CPC . *C12R 1/19* (2013.01); *C12P 13/04* (2013.01); *C12N 9/0024* (2013.01); *C12N 9/86* (2013.01); *C12N 9/90* (2013.01); *C12P 41/009* (2013.01)

(58) Field of Classification Search
CPC .......... C12R 1/19; C12P 13/04; C12P 41/009; C12N 1/20; C12N 9/90; C12N 9/0024; C12N 9/86
USPC .......... 435/252.33, 106, 107, 108, 110, 252.3
See application file for complete search history.

(56) References Cited

U.S. PATENT DOCUMENTS 5,728,555 A * 3/1998 Fotheringham et al. ....... 435/106
5,877,003 A * 3/1999 Grifantini et al. ............ 435/228

FOREIGN PATENT DOCUMENTS

DE 101 14 999 10/2002

OTHER PUBLICATIONS

Chica et al. (Curr Opin Biotechnol. Aug. 2005; 16(4):378-84.*
Ley et al. Org. lett. May 2002, 711-714.*
Expasy D-carbamoylase, EC 3.5.1.77.*
Expasy—Hydantoinase: EC 3.5.2.2.*
Nagata et al. Biochem. J. 1989, 257, pp. 291-292.*
Marceau, Michelle et al. "D-Serine Dehydratase from *Escherichia coli*", Journal of Biological Chemistry, vol. 263, No. 32, pp. 16926-16933, XP002272606, 1988.
Wild, Jadwiga et al. "D-Amino Acid Dehydrogenase of *Escherichia coli* K12: Positive Selection of Mutants Defective in Enzyme Activity and Localization of the Structural Gene", Mol. Gen. Genet., vol. 181. No. 3, pp. 373-378, XP009027160 1981.
Sareen, Dipti et al. "Chaperone-Assisted Overexpression of an Active D-Carbamoylase from Agrobacterium tumefaciens AM 10", Protein Expression and Purification, vol. 23, No. 3, pp. 374-379, XP002272608, 2001.
Hils, M. et al. "Cloning and characterization of genes from *Agrobacterium* sp. IP I-671 involved in hydantoin degradation", Appl. Microbiol. Biotechnol., vol. 57, No. 5/6, pp. 680-688, XP001118705, 2001.
Lobocka, Malgorzata et al. "Organization and Expression of the *Escherichia coli* K-12 dad Operon Encoding the Smaller Subunit of D-Amino Acid Dehydrogenase and the Catabolic Alanine Racemase", Journal of Bacteriology, vol. 176, No. 5, pp. 1500-1510, XP009027210, 1994.
Datsenko, Kirill A. et al. "One-step inactivation of chromosomal genes in *Escherichia coli* K-12 using PCR products", PNAS, vol. 97, No. 12, pp. 6640-6645, XP002210218, 2000.
Alexeyev, Mikhail F. et al. "The pKNOCK Series of Broad-Host-Range Mobilizable Suicide Vectors for Gene Knockout and Targeted DNA Insertion into the Chromosome of Gram-Negative Bacteria", Biotechniques, vol. 26, No. 5, pp. 824-828, XP001179978, 1999.
Marceau, et al., (JBC 1988 pp. 16926-16933).

* cited by examiner

*Primary Examiner* — Tekchand Saidha
*Assistant Examiner* — Md. Younus Meah
(74) *Attorney, Agent, or Firm* — Oblon, McClelland, Maier & Neustadt, L.L.P.

(57) ABSTRACT

*Escherichia. coli* mutants which can be used for the synthesis of D-amino acids, and to such a process. The mutants are distinguished by deficiencies in particular enzymes which break down D-amino acids and include those which produce D-amino acids via the carbamoylase/hydantoinase route.

15 Claims, 2 Drawing Sheets

MUTANTS FOR THE PREPARATION OF D-AMINO ACIDS

This application is a continuation of U.S. application Ser. No. 10/527,061, filed Mar. 9, 2005 (now abandoned) which is a national-stage filing of PCT/EP03/11432, filed Oct. 15, 2003.

The present invention relates to a process for the preparation of D-amino acids. In particular, these are obtained enzymatically via the so-called hydantoinase route using recombinant microorganisms. The present invention likewise relates to microorganisms modified in this way.

D-Amino acids are compounds which are often employed in organic synthesis as intermediates for the preparation of pharmaceutical active compounds.

Enzymatic hydrolysis of 5-substituted hydantoins to give N-carbamoyl-amino acids and further reaction thereof to give the corresponding enantiomerically enriched amino acids is a standard method in organic chemistry ("Enzyme Catalysis in Organic Synthesis", eds.: Drauz, Waldmann, VCH, 1st and 2nd ed.). The enantiodifferentiation can take place here either at the stage of hydantoin hydrolysis by hydantoinases, or optionally during cleavage of N-carbamoylamino acids by means of enantioselective carbamoylases. Since the enzymes in each case convert only one optical antipode of the corresponding compound, attempts are made to racemize the other in the mixture (in situ) in order to ensure complete conversion of the racemic hydantoin, which is easy to prepare, into the corresponding enantiomerically enriched amino acid. The racemization can take place here either at the stage of the hydantoins by means of chemical (base, acid, elevated temp.) or enzymatic processes, or can proceed at the stage of the N-carbamoylamino acids by means of e.g. acetylamino acid racemases (DE10050124). The latter variant of course functions successfully only if enantioselective carbamoylases are employed. The following equation illustrates this state of affairs.

Equation 1:

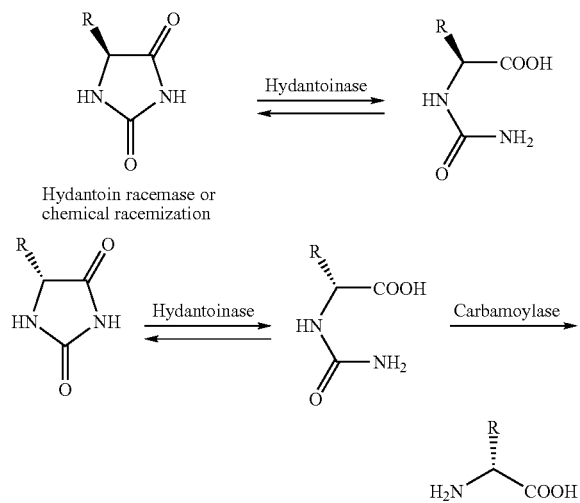

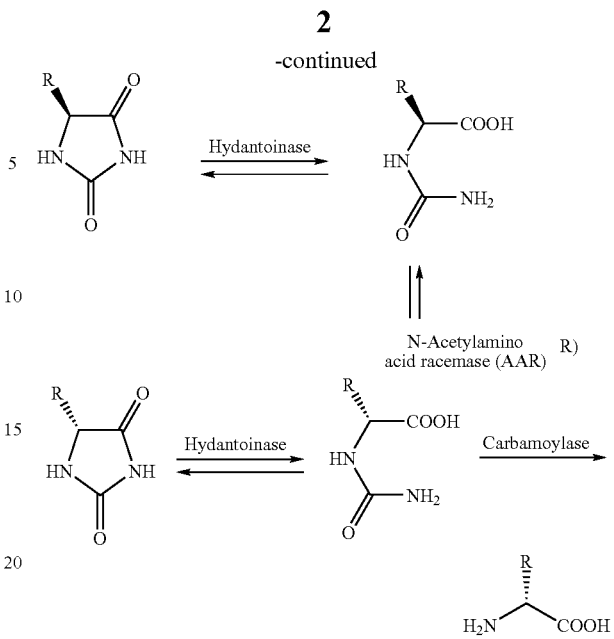

It has been found that the use of recombinant microorganisms which have hydantoinase, carbamoylase and racemase activities for the preparation of various D-amino acids presents problems. FIG. 1 shows the conversion of hydroxymethylhydantoin and ethylhydantoin with *E. coli* JM109 transformed with a D-carbamoylase and D-hydantoinase from *Arthrobacter crystallopoietes* DSM 20117 (in accordance with the patent application DE10114999.9 and DE10130169.3). The reaction conditions are chosen according to example 1.

As FIG. 1 shows by way of example, in the conversion of various 5-monosubstituted hydantoins, marked breakdown of the D-amino acids formed takes place. This reduces the yield which can be achieved and makes working up of the product difficult.

The expert knows that various enzymes, such as D-amino acid oxidases [EC 1.4.3.3], D-amino acid dehydrogenases [EC 1.4.99.1], D-amino acid aminotransferases [EC 2.6.1.21], D-amino acid N-acetyltransferases [EC 2.3.1.36], D-hydroxyamino acid dehydratases [EC 4.2.1.14] and D-amino acid racemases [EC 5.1.1.10] can participate in the breakdown of D-amino acids. Various methods for inactivating these genes in a targeted or also non-targeted manner are also known to the expert [The PKNOCK series of broad-host-range mobilizable suicide vectors for gene knockout and targeted DNA insertion into the chromosome of Gram-negative bacteria. Alexeyev, Mikhail F. BioTechniques (1999), 26(5), 824-828; One-step inactivation of chromosomal genes in *Escherichia coli* K-12 using PCR products, Datsenko, Kirill A. and Wanner, Barry L. PNAS (2000), 97(12), 6640-6645; D-amino acid dehydrogenase of *Escherichia coli* K12: positive selection of mutants defective in enzyme activity and localization of the structural gene, Wild, Jadwiga and Klopotowski, T. Mol. Gen. Genet. (1981), 181(3), 373-378.].

Unfortunately, however, the effect to be expected on cell growth when the various enzymes are inactivated is unknown and unforeseeable. What enzyme or whether a combination of various enzymes has to be inactivated in order to reduce the breakdown of a particular D-amino acid to the desired extent also cannot be predicted.

The object of the present invention was therefore to provide a microorganism which is capable of production of D-amino acids via the carbamoylase/hydantoinase route and helps to render possible a higher yield of D-amino acid produced. It should be possible to employ this advantageously on an industrial scale under economic and ecological aspects. In particular, it should have very good growth properties under the usual economically appropriate conditions, and a sufficient genetic and physical stability and a sufficiently fast rate of conversion for hydantoins.

This object is achieved according to the following embodiments of the invention. Embodiments 1 to 5 relate to particular microorganisms modified in this way. Embodiment 1 refers to a recombinant microorganism for the preparation of D-amino acids starting from N-carbamoylamino acids or 5-monosubstituted hydantoins in which the gene which codes for a D-amino acid oxidase and/or the gene which codes for a D-serine dehydratase is inactivated by mutagenesis; Embodiments 2-5 track Embodiment 1 where, respectively, the recombinant microorganism is an organism of the genus *Escherichia coli*, the recombinant microorganism has a D-carbamoylase gene from *Agrobacterium* sp., *Arthrobacter* sp. or *Bacillus* sp., or where the recombinant microorganism is *Escherichia coli* DSM 15181 or DSM 15182 or mutants derived from these strains. Embodiments 6 and 7 refer to a process for the preparation of D-amino acids where, respectively, the recombinant microorganism according to Embodiment 1 is utilized, and wherein D-aminobutyric acid, D-serine, D-methionine, D-tryptophan and D-phenylalanine are prepared.

Figure 1:
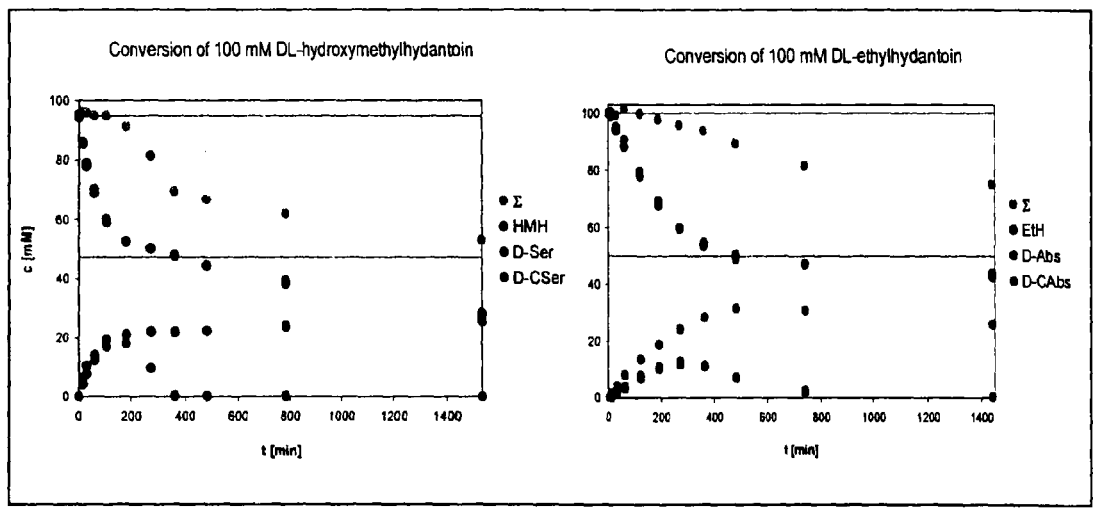
FIG. 1 shows the conversion of hydroxymethylhydantoin and ethylhydantoin with *E. coli* JM109 transformed with a D-carbamoylase and D-hydantoinase from *Arthrobacter crystallopoietes* DSM 20117.

By providing a recombinant microorganism for the preparation of D-amino acids starting from N-carbamoylamino acids or 5-monosubstituted hydantoins in which the gene which codes for a D-amino acid oxidase and/or the gene which codes for a D-serine dehydratase is inactivated by mutagenesis, the objects mentioned are surprisingly and nevertheless advantageously achieved. In particular, it is to be considered surprising that microorganisms with the gene profile according to the invention which have been produced by a recombinant method are in fact stable and are capable of producing D-amino acids to an extent sufficient for industrial orders of size.

Microorganisms for recombinant embodiments which can be used are in principle all the organisms possible to the expert for this purpose, such as fungi, e.g. *Aspergillus* sp., *Streptomyces* sp., *Hansenula polymorpha*, *Pichia pastoris* and *Saccharomyces cerevisiae*, or also prokaryotes, such as *E. coli* and *Bacillus* sp. Microorganisms of the genus *Escherichia coli* can be regarded as preferred microorganisms according to the invention.

The following are very particularly preferred: *E. coli* XL1 Blue, NM 522, JM101, JM109, JM105, BL21, W3110, RR1, DH5α, TOP 10⁻ or HB101. Organisms modified in this way can be produced by methods familiar to the expert. This serves to multiply and produce a sufficient amount of the recombinant enzymes. The processes for this are well-known to the expert (Sambrook, J.; Fritsch, E. F. and Maniatis, T. (1989), Molecular cloning: a laboratory manual, 2nd ed., Cold Spring Harbor Laboratory Press, New York).

The said nucleic acid sequences are thus cloned into a host organism with plasmids or vectors by known methods and the polypeptides expressed in this way can be detected with suitable screening methods. All the possible detection reactions for the molecules formed are in principle suitable for the detection. In particular, detection reactions which are suitable in principle are all the possible detection reactions for ammonia and ammonium ions, such as Nessler reagent (Vogel, A., I., (1989) Vogel's textbook of quantitative chemical analysis, John Wiley & Sons, Inc., 5th ed., 679-698, New York), the indophenol reaction, also called Berthelot's reaction (Wagner, R., (1969) Neue Aspekte zur Stickstoffanalytik in der Wasserchemie, Vom Wasser, VCH-Verlag, vol. 36, 263-318, Weinheim), in particular enzymatic determination by means of glutamate dehydrogenase (Bergmeyer, H., U., and Beutler, H.-O. (1985) Ammonia, in: Methods of Enzymatic Analysis, VCH-Verlag, $3^{rd}$ edition, vol. 8: 454-461, Weinheim) and also detection with ammonium-sensitive electrodes. HPLC methods are furthermore used for detection of amino acids, such as e.g. a derivative method based on o-pthaldialdehyde and N-isobutyryl-cysteine for enantiomer separation of amino acids (Bruckner, H., Wittner R., and Godel H., (1991), Fully automated high-performance liquid chromatographic separation of DL-amino acids derivatized with o-Phthaldialdehyde together with N-isopropyl-cysteine. Application to food samples, Anal. Biochem. 144, 204-206).

Possible plasmids or vectors are in principle all the embodiments available to the expert for this purpose. Such plasmids and vectors can be found e.g. in Studier and colleagues (Studier, W. F.; Rosenberg A. H.; Dunn J. J.; Dubendroff J. W.; (1990), Use of the T7 RNA polymerase to direct expression of cloned genes, Methods Enzymol. 185, 61-89) or the brochures of Novagen, Promega, New England Biolabs, Clontech or Gibco BRL. Further preferred plasmids and vectors can be found in: Glover, D. M. (1985), DNA cloning: A Practical Approach, vol. I-III, IRL Press Ltd., Oxford; Rodriguez, R. L. and Denhardt, D. T (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, $2^{nd}$ ed., Cold Spring Harbor Laboratory Press, New York. Particularly preferred cloning vectors of D-carbamoylases in *E. coli* are, for example, derivatives of pBR322, pACYC184, pUC18 or pSC101, which can carry constitutive and also inducible promoters for expression control. Particularly preferred promoters are lac, tac, trp, trc, T3, T5, T7, rhaBAD, araBAD, □pL and phoA promoters, which are sufficiently known to the expert [Strategies for achieving high-level expression of genes in *Escherichia coli*, Makrides S. C. Microbiol. Rev. 60(3), 512-538].

The inactivation of the D-amino acid oxidase (dadA) or D-serine dehydratase (dsdA) of these organisms is carried out here by methods described above, which are known to the expert. For production of the recombinant embodiments of the D-serine dehydratase- or D-amino acid oxidase-deficient strains with D-carbamoylase activity, the fundamental molecular biology methods are thus known to the expert (Sambrook, J.; Fritsch, E. F. and Maniatis, T. (1989), Molecular cloning: a laboratory manual, 2nd ed., Cold Spring Harbor Laboratory Press, New York). Gene sequences of various D-carbamoylases e.g. from *Agrobacterium* sp., *Arthrobacter* sp. or *Bacillus* sp. and *Ralstonia pickettii*, which are preferably used, are likewise known (inter alia from U.S. Pat. No. 5,858,759, U.S. Pat. No. 5,807,710, U.S. Pat. No. 6,083,752, U.S. Pat. No. 6,083,752, U.S. Pat. No. 6,083,752, U.S. Pat. No. 6,083,752, U.S. Pat. No. 6,083,752).

The same methods can be used for the production of organisms which additionally contain a hydantoinase and optionally a hydantoin or carbamoyl racemase. Preferred hydantoinases which are to be employed here are those from *Thermus* sp., *Bacillus* sp., *Mycobacterium* sp., *Corynebacterium* sp., *Agrobacterium* sp., *E. coli*, *Burkholderia* sp., *Pseudomonas* sp., or *Arthrobacter* sp. Hydantoin racemase can preferably be used from *Pseudomonas* sp., *Arthrobacter* sp., or *Agrobacterium* sp., optionally with the addition of auxiliary substances, such as metal ions, for example $Mn^{2+}$ ions.

It was thus possible to produce the successful mutants *Escherichia coli* DSM 15181 and *Escherichia coli* DSM 15182. These therefore form, together with the further mutants which can be derived from them, the next subject matter of the present invention.

In the process which is likewise according to the invention, e.g. a hydantoin is converted with the said cells or cell constituents in a suitable solvent, such as, for example, water, to which further water-soluble or water-insoluble organic solvents can be added, at pH values of between 6.0 and 11, preferably between 7 and 10, and a temperature of between 10° C. and 100° C., preferably between 30° C. and 70° C., particularly preferably between 37° C. and 60° C. The enzymes in question can also be used in the free form for the use. The enzymes can furthermore also be employed as a constituent of an intact guest organism or in combination with the broken-down cell mass of the host organism, which has been purified to any desired extent. It is also possible to use the recombinant cells in flocculated, cross-linked or immobilized form, for example using agar, agarose, carrageenan, alginates, pectins, chitosan, polyacrylamides and other synthetic carriers (Chemical aspects of immobilized systems in biotechnologies. Navratil, Marian; Sturdik, Ernest. Chemicke Listy (2000), 94(6), 380-388; Industrial applications of immobilized biocatalysts and biomaterials. Chibata, Ichiro. Advances in Molecular and Cell Biology (1996), 15A (Biochemical Technology), 151-160; Immobilization of genetically engineered cells: a new strategy for higher stability. Kumar, P. K. R.; Schuegerl, K. Journal of Biotechnology (1990), 14(3-4), 255-72.).

A process for the preparation of D-amino acids with a microorganism according to the invention accordingly forms the next subject matter of the invention. D-Aminobutyric acid, D-serine, D-methionine, D-tryptophan and D-phenylalanine are preferably prepared.

Organisms with D-carbamoylase-active and hydantoinase-active and dadA-inactivated and/or dsdA-inactivated cells are preferably used in this process for the preparation of D-amino acids. It should be mentioned here that both L-, D- or DL-carbamoylamino acids and 5-monosubstituted hydantoins, which can be converted into the corresponding carbamoylamino acids via sufficiently known hydantoinases, are possible as the educt ("Enzyme Catalysis in Organic Synthesis", eds.: Drauz, Waldmann, VCH, 1$^{st}$ and 2$^{nd}$ ed.). The dadA- and/or dsdA-deficient strains used can co-express here the carbamoylase and hydantoinase, optionally also a hydantoin racemase or carbamoylamino acid racemase, and can be employed either in the free or in the immobilized form (see above).

Figure 2:
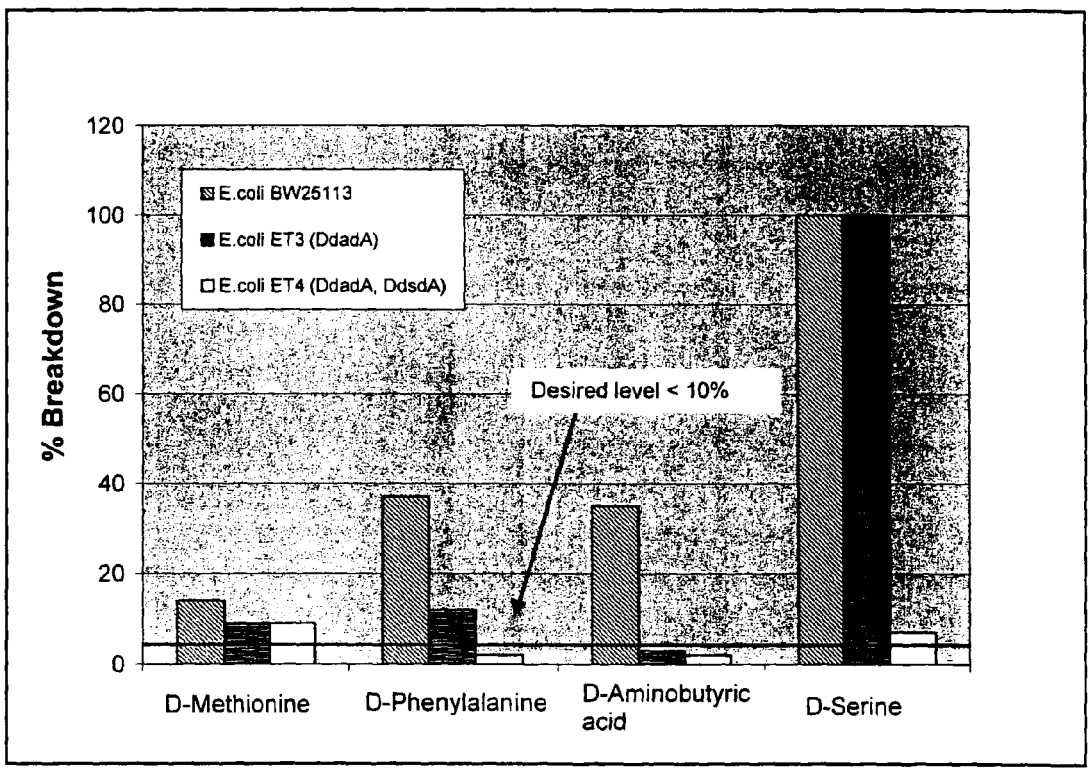
FIG. 2 compares the % breakdown of four different amino acids by *E. coli* strains BW25113, ET3 (DdadA) and ET4 (DdadA, DdsdA)

As has now been found, the inactivation of various enzymes is necessary in order to reduce the breakdown to a sufficient extent (<10% breakdown within >10 hours) for various D-amino acids (see FIG. 2). For the breakdown of D-serine it has been found, surprisingly, that the inactivation of the gene of the D-amino acid oxidase (dadA) is not sufficient to reduce breakdown thereof effectively. For an effective reduction in the breakdown of this amino acid, D-serine hydratase had to be additionally inactivated. In contrast to this, it had been reported in the literature that a breakdown of D-serine reduced >3-fold is achieved by an inactivation of dadA [D-Amino acid dehydrogenase of *Escherichia coli* K12: positive selection of mutants defective in enzyme activity and localization of the structural gene. Wild, J.; Klopotowski, T. Mol. Gen. Genet. (1981), 181(3), 373-378]. Likewise in contrast to the results described there, it has been found, surprisingly, that D-serine is broken down very much faster than, for example, D-methionine.

In contrast to D-serine, the breakdown of aromatic and aliphatic D-amino acids, such as, for example, D-phenylalanine, D-methionine or D-aminobutyric acid, is achieved sufficiently by an inactivation of the D-amino acid oxidase. However, for D-phenylalanine, surprisingly, both deletions (ΔdsdA & ΔdadA) show a positive effect, while for D-methionine the deletion in dsdA shows no additional effect. These results are summarized in FIG. 2 (Breakdown of various amino acids with various mutants of *E. coli* BW25113. *E. coli* ET3 has a deletion of the D-amino acid oxidase (ΔdadA); *E. coli* ET4 additionally has a deletion of D-serine dehydratase (☐dsdA). For the reaction conditions see example 3).

The literature references cited in this specification are regarded as also included in the disclosure.

The organisms DSM15181 (ET3) and DSM15182 (ET4) were deposited under the terms of the Budapest Treaty by Degussa AG on 04.09.2002 at the Deutsche Sammlung für Mikroorganismen und Zellkulturen [German Collection of Microorganisms and Cell Cultures], Mascheroder Weg 1b D-38124 Braunsweig, Germany.

EXAMPLES

Example 1

Production of D-Amino Acids by Means of Recombinant *E. coli* Cells

Figure 3:
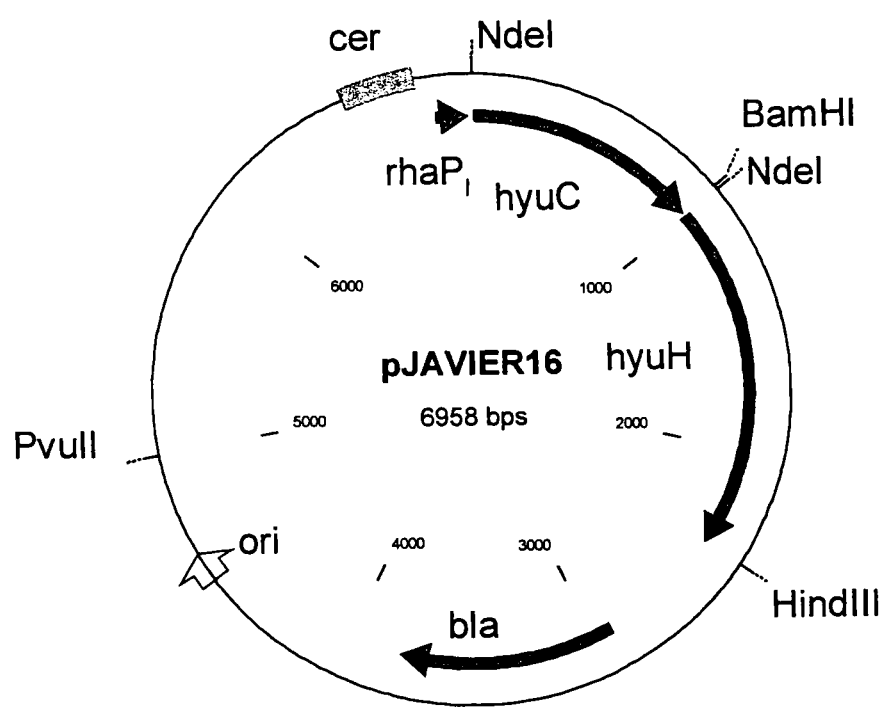
FIG. 3 shows a restriction site map of plasmid pJAVIER16.

Chemically competent *E. coli* JM109 (Promega) were transformed with pJAVI16 (see FIG. 3). This plasmid carries a D-carbamoylase and a D-hydantoinase from *Arthrobacter crystallopoietes* DSM20117. The polynucleotide sequences encoding D-hydantoinase and D-carbamoylase are shown in SEQ ID NOS: 1 and 3 (see also DE10114999.9 and DE10130169.3) and the corresponding encoded proteins by SEQ ID NOS: 2 and 4, respectively.

The *E. coli* cells transformed with pJAVIER16 were placed individually on LBamp plates (ampicillin concentration: 100 μg/ml). 2.5 ml LBamp medium with 1 mM $ZnCl_2$ were inoculated with an individual colony and incubated for 30 hours at 37° C. and 250 rpm. This culture was diluted 1:50 in 100 ml LBamp medium with 1 mM $ZnCl_2$ and 2 g/l rhamnose and incubated for 18 h at 30° C. The culture was centrifuged for 10 min at 10,000 g, the supernatant was discarded and the biomass was weighed. Various hydantoin derivatives, e.g. 100 mM DL-hydroxymethylhydantoin or DL-ethylhydantoin, pH 7.5, were added to the biomass so that a biomass concentration of 40 g moist biomass per liter results. The reaction solution was incubated at 37° C. After various periods of time, samples were taken and centrifuged and the amino acids formed were quantified by means of HPLC.

Example 2

Production of DsdA- and DadA-Deficient *E. coli* Strains

DadA was deleted in *E. coli* BW25113 (deposited at CGSC under number CGSC7636) by the method described by Datsenko & Wanner (One-step inactivation of chromosomal genes in *Escherichia coli* K-12 using PCR products, Datsenko, Kirill A. and Wanner, Barry L. PNAS (2000), 97(12), 6640-6645). The following primers were used for this for amplification of the chloramphenicol resistance from pKD13 (deposited at CGSC under number CGSC7633):

```
                                              (SEQ ID NO: 5)
5'_AACCAGTGCCGCGAATGCCGGGCAAATCTCCCCCGGATATGCTGCAC
CGTATTCCGGGGATCCGTCGACC_3':
                                              (SEQ ID NO: 6)
5'_AGGGGTACCGGTAGGCGCGTGGCGCGGATAACCGTCGGCGATTCCG
GGGATCCGTCGACC-3':
```

A transformation of the amplified product in *E. coli* BW25113 (pKD46) (deposited at CGSC under number CGSC7630) and selection of kanamycin-resistant clones rendered possible the isolation of *E. coli* ET2. After removal of the chloramphenicol resistance in accordance with the protocol of Datsenko & Wanner, it was possible to isolate the strain *E. coli* ET3. For the deletion of dsdA in *E. coli* ET3, the chloramphenicol resistance from pKD13 was in turn amplified with the following primers:

```
                                              (SEQ ID NO: 7)
5'_GCGGGCACATTCCTGCTGTCATTTATCATCTAAGCGCAAAGAGACGT
ACTGTGTAGGCTGGAGCTGCTTC_3':
                                              (SEQ ID NO: 8)
5'_GCAGCATCGCTCACCCAGGGAAAGGATTGCGATGCTGCGTTGAAACG
TTAATGGGAATTAGCCATGGTCC_3':
```

Transformation of the amplified product in *E. coli* ET3 (pKD46) and selection of kanamycin-resistant clones rendered possible the isolation of *E. coli* ET4, which carries a deletion both in dadA and in dsdA.

Example 3

Investigation of the Breakdown of D-Amino Acids 2.5 ml LB medium were inoculated with an individual colony of *E. coli* BW25113, *E. coli* ET3 and *E. coli* ET4 and incubated for 18 hours at 37° C. and 250 rpm. These cultures were diluted 1:50 in 100 ml LB medium and incubated for 18 h at 37° C. The cultures were centrifuged for 10 min at 10,000 g, the supernatant was discarded and the biomass was weighed. Various 100 mM D-amino acid solutions, pH 7.5 (e.g. D-methionine, D-phenylalanine, D-aminobutyric acid, D-serine) were added to the biomass so that a biomass concentration of 100 g moist biomass per liter results. These reaction solutions were incubated at 37° C. and centrifuged after 10 hours. The clear supernatant was analysed for the remaining amino acid concentration by means of HPLC. The % breakdown stated was calculated from the quotient of the starting concentration and the final concentration after incubation for 10 hours.

The invention claimed is:

1. An isolated *Escherichia coli* strain
having its dadA gene mutated or deleted so that said gene does not express a functional D-amino acid oxidase; and
having its dsdA gene mutated or deleted so that said gene does not express a functional D-serine dehydratase;
wherein said strain has been transformed with and expresses a D-carbamoylase gene and a D-hydantoinase gene,
wherein the strain is *Escherichia coli* strain DSM15182 (ET4), and
wherein the isolated strain exhibits reduced breakdown of produced D-amino acids when cultured in a suitable medium.

2. A process for preparing a D-amino acid comprising:
culturing in a suitable medium the isolated *Escherichia coli* strain of claim 1, and
recovering a D-amino acid,
wherein the isolated strain exhibits reduced breakdown of produced D-amino acids when cultured.

3. The process of claim 2, wherein the D-amino acid that is recovered is D-serine.

4. The process of claim 2, wherein the D-amino acid that is recovered is D-methionine.

5. The process of claim 2, wherein the D-amino acid that is recovered is D-tryptophan.

6. The process of claim 2, wherein the D-amino acid that is recovered is D-phenylalanine.

7. The process of claim 2, wherein the D-amino acid that is recovered is D-aminobutyric acid.

8. A method for producing a D-amino acid via the carbamoylase/hydantoinase route comprising culturing an isolated microorganism that has been transformed with and expresses a D-carbamoylase gene and a D-hydantoinase gene;
wherein said microorganism lacks at least one gene that expresses a functional D-amino oxidase and D-amino acid dehydratase;
wherein said microorganism is selected from the group consisting of *Escherichia coli* DCM15181 (ET3) and *Escherichia coli* DSM15182 (ET4), and
wherein the isolated strain exhibits reduced breakdown of produced D-amino acids when cultured.

9. The isolated *Escherichia coli* strain of claim 1, wherein the isolated strain exhibits reduced breakdown of produced D-amino acids to less than 10% when cultured for at least 10 hours.

10. The process of claim 2, wherein the isolated strain exhibits reduced breakdown of produced D-amino acids to less than 10% when cultured for at least 10 hours.

11. The process of claim 8, wherein the isolated strain exhibits reduced breakdown of produced D-amino acids to less than 10% when cultured for at least 10 hours.

12. The isolated *Escherichia coli* strain of claim 1, wherein the amino acid breakdown provided by the isolated strain is less than an amino acid breakdown provided by a strain which has unaltered dadA and dsdA genes.

13. The process of claim 2, wherein the amino acid breakdown provided by the isolated strain is less than an amino acid breakdown provided by a strain which has unaltered dadA and dsdA genes.

14. The method of claim 8, wherein the amino acid breakdown provided by the isolated strain is less than an amino acid breakdown provided by a strain which has unaltered dadA and dsdA genes.

15. An isolated *Escherichia coli* strain that has been transformed with and expresses a D-carbamoylase gene and a D-hydantoinase gene;
wherein said strain is *Escherichia coli* DCM15181 (ET3) that lacks a dadA gene that expresses a functional D-amino oxidase.

\* \* \* \* \*

SEQUENCE LISTING

```
<160> NUMBER OF SEQ ID NOS: 8

<210> SEQ ID NO 1
<211> LENGTH: 948
<212> TYPE: DNA
<213> ORGANISM: Arthrobacter crystallopoietes
<220> FEATURE:
<221> NAME/KEY: CDS
<222> LOCATION: (1)..(948)

<400> SEQUENCE: 1 atg gcg aaa aac ttg atg ctc gcg gtc gct caa gtc ggc ggt atc gat      48
Met Ala Lys Asn Leu Met Leu Ala Val Ala Gln Val Gly Gly Ile Asp
1               5                  10                  15 agt tcg gaa tca aga ccc gaa gtc gtc gcc cgc ttg att gcc ctg ctg      96
Ser Ser Glu Ser Arg Pro Glu Val Val Ala Arg Leu Ile Ala Leu Leu
            20                  25                  30 gaa gaa gca gct tcc cag ggc gcg gaa ctg gtg gtc ttt ccc gaa ctc     144
Glu Glu Ala Ala Ser Gln Gly Ala Glu Leu Val Val Phe Pro Glu Leu
        35                  40                  45 acg ctg acc acg ttc ttc ccg cgt acc tgg ttc gaa gaa ggc gac ttc     192
Thr Leu Thr Thr Phe Phe Pro Arg Thr Trp Phe Glu Glu Gly Asp Phe
    50                  55                  60 gag gaa tac ttc gat aaa tcc atg ccc aat gac gac gtc gcg ccc ctt     240
Glu Glu Tyr Phe Asp Lys Ser Met Pro Asn Asp Asp Val Ala Pro Leu
65                  70                  75                  80 ttc gaa cgc gcc aaa gac ctt ggc gtg ggc ttc tac ctc gga tac gcg     288
Phe Glu Arg Ala Lys Asp Leu Gly Val Gly Phe Tyr Leu Gly Tyr Ala
                85                  90                  95
```

-continued

| | | |
|---|---|---|
| gaa ctg acc agt gat gag aag cgg tac aac aca tca att ctg gtg aac<br>Glu Leu Thr Ser Asp Glu Lys Arg Tyr Asn Thr Ser Ile Leu Val Asn<br>              100                 105                 110 | | 336 |
| aag cac ggc gac atc gtc ggc aag tac cgc aag atg cat ctg ccg ggc<br>Lys His Gly Asp Ile Val Gly Lys Tyr Arg Lys Met His Leu Pro Gly<br>          115                 120                 125 | | 384 |
| cac gcc gat aac cgg gaa gga cta ccc aac cag cac ctt gaa aag aaa<br>His Ala Asp Asn Arg Glu Gly Leu Pro Asn Gln His Leu Glu Lys Lys<br>      130                 135                 140 | | 432 |
| tac ttc cgc gaa gga gat ctc gga ttc ggt gtc ttc gac ttc cac ggc<br>Tyr Phe Arg Glu Gly Asp Leu Gly Phe Gly Val Phe Asp Phe His Gly<br>145                 150                 155                 160 | | 480 |
| gtg cag gtc gga atg tgt ctc tgc aac gac cgg cga tgg ccg gag gtc<br>Val Gln Val Gly Met Cys Leu Cys Asn Asp Arg Arg Trp Pro Glu Val<br>                  165                 170                 175 | | 528 |
| tac cgc tct ttg gcc ctg cag gga gca gag ctc gtc gtc ctg ggc tac<br>Tyr Arg Ser Leu Ala Leu Gln Gly Ala Glu Leu Val Val Leu Gly Tyr<br>              180                 185                 190 | | 576 |
| aac acc ccc gat ttc gtt ccc ggc tgg cag gaa gag cct cac gcg aag<br>Asn Thr Pro Asp Phe Val Pro Gly Trp Gln Glu Glu Pro His Ala Lys<br>          195                 200                 205 | | 624 |
| atg ttc acg cac ctt ctt tca ctt cag gca ggg gca tac cag aac tcg<br>Met Phe Thr His Leu Leu Ser Leu Gln Ala Gly Ala Tyr Gln Asn Ser<br>      210                 215                 220 | | 672 |
| gta ttt gtg gcg gct gcc ggc aag tcg ggc ttc gaa gac ggg cac cac<br>Val Phe Val Ala Ala Ala Gly Lys Ser Gly Phe Glu Asp Gly His His<br>225                 230                 235                 240 | | 720 |
| atg atc ggc gga tca gcg gtc gcc gcg ccc agc ggc gaa atc ctg gca<br>Met Ile Gly Gly Ser Ala Val Ala Ala Pro Ser Gly Glu Ile Leu Ala<br>                  245                 250                 255 | | 768 |
| aaa gca gcc ggc gag ggc gat gaa gtc gtc gtt gtg aaa gca gac atc<br>Lys Ala Ala Gly Glu Gly Asp Glu Val Val Val Val Lys Ala Asp Ile<br>              260                 265                 270 | | 816 |
| gac atg ggc aag ccc tat aag gaa agc gtc ttc gac ttc gcc gcc cat<br>Asp Met Gly Lys Pro Tyr Lys Glu Ser Val Phe Asp Phe Ala Ala His<br>          275                 280                 285 | | 864 |
| cgg cgc ccc gac gca tac ggc atc atc gcc gaa agg aaa ggg cgg ggc<br>Arg Arg Pro Asp Ala Tyr Gly Ile Ile Ala Glu Arg Lys Gly Arg Gly<br>      290                 295                 300 | | 912 |
| gcc cca ctg ccc gtc ccg ttc aac gtg aat gac taa<br>Ala Pro Leu Pro Val Pro Phe Asn Val Asn Asp<br>305                 310                 315 | | 948 |

<210> SEQ ID NO 2
<211> LENGTH: 315
<212> TYPE: PRT
<213> ORGANISM: Arthrobacter crystallopoietes

<400> SEQUENCE: 2

Met Ala Lys Asn Leu Met Leu Ala Val Ala Gln Val Gly Gly Ile Asp
1               5                   10                  15

Ser Ser Glu Ser Arg Pro Glu Val Val Ala Arg Leu Ile Ala Leu Leu
                20                  25                  30

Glu Glu Ala Ala Ser Gln Gly Ala Glu Leu Val Val Phe Pro Glu Leu
            35                  40                  45

Thr Leu Thr Thr Phe Phe Pro Arg Thr Trp Phe Glu Glu Gly Asp Phe
        50                  55                  60

Glu Glu Tyr Phe Asp Lys Ser Met Pro Asn Asp Asp Val Ala Pro Leu
65                  70                  75                  80

-continued

```
Phe Glu Arg Ala Lys Asp Leu Gly Val Gly Phe Tyr Leu Gly Tyr Ala
                85                  90                  95

Glu Leu Thr Ser Asp Glu Lys Arg Tyr Asn Thr Ser Ile Leu Val Asn
            100                 105                 110

Lys His Gly Asp Ile Val Gly Lys Tyr Arg Lys Met His Leu Pro Gly
        115                 120                 125

His Ala Asp Asn Arg Glu Gly Leu Pro Asn Gln His Leu Glu Lys Lys
    130                 135                 140

Tyr Phe Arg Glu Gly Asp Leu Gly Phe Gly Val Phe Asp Phe His Gly
145                 150                 155                 160

Val Gln Val Gly Met Cys Leu Cys Asn Asp Arg Arg Trp Pro Glu Val
                165                 170                 175

Tyr Arg Ser Leu Ala Leu Gln Gly Ala Glu Leu Val Leu Gly Tyr
            180                 185                 190

Asn Thr Pro Asp Phe Val Pro Gly Trp Gln Glu Pro His Ala Lys
        195                 200                 205

Met Phe Thr His Leu Leu Ser Leu Gln Ala Gly Ala Tyr Gln Asn Ser
    210                 215                 220

Val Phe Val Ala Ala Gly Lys Ser Gly Phe Glu Asp Gly His His
225                 230                 235                 240

Met Ile Gly Gly Ser Ala Val Ala Ala Pro Ser Gly Glu Ile Leu Ala
                245                 250                 255

Lys Ala Ala Gly Glu Gly Asp Glu Val Val Val Lys Ala Asp Ile
            260                 265                 270

Asp Met Gly Lys Pro Tyr Lys Glu Ser Val Asp Phe Ala Ala His
        275                 280                 285

Arg Arg Pro Asp Ala Tyr Gly Ile Ile Ala Glu Arg Lys Gly Arg Gly
    290                 295                 300

Ala Pro Leu Pro Val Pro Phe Asn Val Asn Asp
305                 310                 315

<210> SEQ ID NO 3
<211> LENGTH: 1404
<212> TYPE: DNA
<213> ORGANISM: Arthrobacter crystallopoietes
<220> FEATURE:
<221> NAME/KEY: CDS
<222> LOCATION: (1)..(1404)

<400> SEQUENCE: 3 atg gat gca aag cta ctg gtt ggc ggc act att gtt tcc tcg acc ggc      48
Met Asp Ala Lys Leu Leu Val Gly Gly Thr Ile Val Ser Ser Thr Gly
1               5                   10                  15 aaa atc cga gcc gac gtg ctg att gaa aac ggc aaa gtc gcc gct gtc      96
Lys Ile Arg Ala Asp Val Leu Ile Glu Asn Gly Lys Val Ala Ala Val
                20                  25                  30 ggc atg ctg gac gcc gcg acg ccg gac aca gtt gag cgg gtt gac tgc     144
Gly Met Leu Asp Ala Ala Thr Pro Asp Thr Val Glu Arg Val Asp Cys
            35                  40                  45 gac ggc aaa tac gtc atg ccc ggc ggt atc gac gtt cac acc cac atc     192
Asp Gly Lys Tyr Val Met Pro Gly Gly Ile Asp Val His Thr His Ile
        50                  55                  60 gac tcc ccc ctc atg ggg acc acc acc gcc gat gat ttt gtc agc gga     240
Asp Ser Pro Leu Met Gly Thr Thr Thr Ala Asp Asp Phe Val Ser Gly
65                  70                  75                  80 acg att gca gcc gct acc ggc gga aca acg acc atc gtc gat ttc gga     288
Thr Ile Ala Ala Ala Thr Gly Gly Thr Thr Thr Ile Val Asp Phe Gly
                85                  90                  95
```

```
cag cag ctc gcc ggc aag aac ctg ctg gaa tcc gca gac gcg cac cac    336
Gln Gln Leu Ala Gly Lys Asn Leu Leu Glu Ser Ala Asp Ala His His
            100                 105                 110 aaa aag gcg cag ggg aaa tcc gtc att gat tac ggc ttc cat atg tgc    384
Lys Lys Ala Gln Gly Lys Ser Val Ile Asp Tyr Gly Phe His Met Cys
            115                 120                 125 gtg acg aac ctc tat gac aat ttc gat tcc cat atg gca gaa ctg aca    432
Val Thr Asn Leu Tyr Asp Asn Phe Asp Ser His Met Ala Glu Leu Thr
        130                 135                 140 cag gac gga atc tcc agt ttc aag gtc ttc atg gcc tac cgc gga agc    480
Gln Asp Gly Ile Ser Ser Phe Lys Val Phe Met Ala Tyr Arg Gly Ser
145                 150                 155                 160 ctg atg atc aac gac ggc gaa ctg ttc gac atc ctc aag gga gtc ggc    528
Leu Met Ile Asn Asp Gly Glu Leu Phe Asp Ile Leu Lys Gly Val Gly
                165                 170                 175 tcc agc ggt gcc aaa cta tgc gtc cac gca gag aac ggc gac gtc atc    576
Ser Ser Gly Ala Lys Leu Cys Val His Ala Glu Asn Gly Asp Val Ile
            180                 185                 190 gac agg atc gcc gcc gac ctc tac gcc caa gga aaa acc ggg ccc ggg    624
Asp Arg Ile Ala Ala Asp Leu Tyr Ala Gln Gly Lys Thr Gly Pro Gly
        195                 200                 205 acc cac gag atc gca cgc ccg ccg gaa tcg gaa gtc gaa gca gtc agc    672
Thr His Glu Ile Ala Arg Pro Pro Glu Ser Glu Val Glu Ala Val Ser
210                 215                 220 cgg gcc atc aag atc tcc cgg atg gcc gag gtg ccg ctg tat ttc gtg    720
Arg Ala Ile Lys Ile Ser Arg Met Ala Glu Val Pro Leu Tyr Phe Val
225                 230                 235                 240 cat ctt tcc acc cag ggg gcc gtc gag gaa gta gct gcc gcg cag atg    768
His Leu Ser Thr Gln Gly Ala Val Glu Glu Val Ala Ala Ala Gln Met
                245                 250                 255 aca gga tgg cca atc agc gcc gaa acg tgc acc cac tac ctg tcg ctg    816
Thr Gly Trp Pro Ile Ser Ala Glu Thr Cys Thr His Tyr Leu Ser Leu
            260                 265                 270 agc cgg gac atc tac gac cag ccg gga ttc gag ccg gcc aaa gct gtc    864
Ser Arg Asp Ile Tyr Asp Gln Pro Gly Phe Glu Pro Ala Lys Ala Val
        275                 280                 285 ctc aca cca ccg ctg cgc aca cag gaa cac cag gac gcg ttg tgg aga    912
Leu Thr Pro Pro Leu Arg Thr Gln Glu His Gln Asp Ala Leu Trp Arg
    290                 295                 300 ggc att aac acc ggt gcg ctc agc gtc gtc agt tcc gac cac tgc ccc    960
Gly Ile Asn Thr Gly Ala Leu Ser Val Val Ser Ser Asp His Cys Pro
305                 310                 315                 320 ttc tgc ttt gag gaa aag cag cgg atg ggg gca gat gac ttc cgg cag   1008
Phe Cys Phe Glu Glu Lys Gln Arg Met Gly Ala Asp Asp Phe Arg Gln
                325                 330                 335 atc ccc aac ggc ggg ccc ggc gtg gag cac cga atg ctc gtg atg tat   1056
Ile Pro Asn Gly Gly Pro Gly Val Glu His Arg Met Leu Val Met Tyr
            340                 345                 350 gag acc ggt gtc gcg gaa gga aaa atg acg atc gag aaa ttc gtc gag   1104
Glu Thr Gly Val Ala Glu Gly Lys Met Thr Ile Glu Lys Phe Val Glu
        355                 360                 365 gtg act gcc gag aac ccg gcc aag caa ttc gat atg tac ccg aaa aag   1152
Val Thr Ala Glu Asn Pro Ala Lys Gln Phe Asp Met Tyr Pro Lys Lys
    370                 375                 380 gga aca att gca ccg ggc tcc gat gca gac atc atc gtg gtc gac ccc   1200
Gly Thr Ile Ala Pro Gly Ser Asp Ala Asp Ile Ile Val Val Asp Pro
385                 390                 395                 400 aac gga aca acc ctc atc agt gcc gac acc caa aaa caa aac atg gac   1248
Asn Gly Thr Thr Leu Ile Ser Ala Asp Thr Gln Lys Gln Asn Met Asp
                405                 410                 415
```

```
tac acg ctg ttc gaa ggc ttc aaa atc cgt tgc tcc atc gac cag gtg    1296
Tyr Thr Leu Phe Glu Gly Phe Lys Ile Arg Cys Ser Ile Asp Gln Val
            420                 425                 430 ttc tcg cgt ggc gac ctg atc agc gtc aaa ggc gaa tat gtc ggc acc    1344
Phe Ser Arg Gly Asp Leu Ile Ser Val Lys Gly Glu Tyr Val Gly Thr
        435                 440                 445 cgc ggc cgc ggc gaa ttc atc aag cgg agc gct tgg agc cac ccg cag    1392
Arg Gly Arg Gly Glu Phe Ile Lys Arg Ser Ala Trp Ser His Pro Gln
450                 455                 460 ttc gaa aaa taa                                                    1404
Phe Glu Lys
465

<210> SEQ ID NO 4
<211> LENGTH: 467
<212> TYPE: PRT
<213> ORGANISM: Arthrobacter crystallopoietes

<400> SEQUENCE: 4

Met Asp Ala Lys Leu Leu Val Gly Gly Thr Ile Val Ser Ser Thr Gly
1               5                   10                  15

Lys Ile Arg Ala Asp Val Leu Ile Glu Asn Gly Lys Val Ala Ala Val
            20                  25                  30

Gly Met Leu Asp Ala Ala Thr Pro Asp Thr Val Glu Arg Val Asp Cys
        35                  40                  45

Asp Gly Lys Tyr Val Met Pro Gly Gly Ile Asp Val His Thr His Ile
    50                  55                  60

Asp Ser Pro Leu Met Gly Thr Thr Thr Ala Asp Phe Val Ser Gly
65                  70                  75                  80

Thr Ile Ala Ala Ala Thr Gly Gly Thr Thr Thr Ile Val Asp Phe Gly
                85                  90                  95

Gln Gln Leu Ala Gly Lys Asn Leu Leu Glu Ser Ala Asp Ala His His
            100                 105                 110

Lys Lys Ala Gln Gly Lys Ser Val Ile Asp Tyr Gly Phe His Met Cys
        115                 120                 125

Val Thr Asn Leu Tyr Asp Asn Phe Asp Ser His Met Ala Glu Leu Thr
    130                 135                 140

Gln Asp Gly Ile Ser Ser Phe Lys Val Phe Met Ala Tyr Arg Gly Ser
145                 150                 155                 160

Leu Met Ile Asn Asp Gly Glu Leu Phe Asp Ile Leu Lys Gly Val Gly
                165                 170                 175

Ser Ser Gly Ala Lys Leu Cys Val His Ala Glu Asn Gly Asp Val Ile
            180                 185                 190

Asp Arg Ile Ala Ala Asp Leu Tyr Ala Gln Gly Lys Thr Gly Pro Gly
        195                 200                 205

Thr His Glu Ile Ala Arg Pro Pro Glu Ser Glu Val Glu Ala Val Ser
    210                 215                 220

Arg Ala Ile Lys Ile Ser Arg Met Ala Glu Val Pro Leu Tyr Phe Val
225                 230                 235                 240

His Leu Ser Thr Gln Gly Ala Val Glu Glu Val Ala Ala Gln Met
                245                 250                 255

Thr Gly Trp Pro Ile Ser Ala Glu Thr Cys Thr His Tyr Leu Ser Leu
            260                 265                 270

Ser Arg Asp Ile Tyr Asp Gln Pro Gly Phe Glu Pro Ala Lys Ala Val
        275                 280                 285
```

```
Leu Thr Pro Pro Leu Arg Thr Gln Glu His Gln Asp Ala Leu Trp Arg
    290                 295                 300

Gly Ile Asn Thr Gly Ala Leu Ser Val Val Ser Ser Asp His Cys Pro
305                 310                 315                 320

Phe Cys Phe Glu Glu Lys Gln Arg Met Gly Ala Asp Phe Arg Gln
                325                 330                 335

Ile Pro Asn Gly Gly Pro Gly Val Glu His Arg Met Leu Val Met Tyr
                340                 345                 350

Glu Thr Gly Val Ala Glu Gly Lys Met Thr Ile Glu Lys Phe Val Glu
            355                 360                 365

Val Thr Ala Glu Asn Pro Ala Lys Gln Phe Asp Met Tyr Pro Lys Lys
    370                 375                 380

Gly Thr Ile Ala Pro Gly Ser Asp Ala Asp Ile Ile Val Val Asp Pro
385                 390                 395                 400

Asn Gly Thr Thr Leu Ile Ser Ala Asp Thr Gln Lys Gln Asn Met Asp
                405                 410                 415

Tyr Thr Leu Phe Glu Gly Phe Lys Ile Arg Cys Ser Ile Asp Gln Val
                420                 425                 430

Phe Ser Arg Gly Asp Leu Ile Ser Val Lys Gly Glu Tyr Val Gly Thr
            435                 440                 445

Arg Gly Arg Gly Glu Phe Ile Lys Arg Ser Ala Trp Ser His Pro Gln
    450                 455                 460

Phe Glu Lys
465

<210> SEQ ID NO 5
<211> LENGTH: 70
<212> TYPE: DNA
<213> ORGANISM: Artificial
<220> FEATURE:
<223> OTHER INFORMATION: Synthetic DNA

<400> SEQUENCE: 5
aaccagtgcc gcgaatgccg ggcaaatctc ccccggatat gctgcaccgt attccgggga      60
tccgtcgacc                                                            70

<210> SEQ ID NO 6
<211> LENGTH: 60
<212> TYPE: DNA
<213> ORGANISM: Artificial
<220> FEATURE:
<223> OTHER INFORMATION: Synthetic DNA

<400> SEQUENCE: 6
aggggtaccg gtaggcgcgt ggcgcggata accgtcggcg attccgggga tccgtcgacc      60

<210> SEQ ID NO 7
<211> LENGTH: 70
<212> TYPE: DNA
<213> ORGANISM: Artificial
<220> FEATURE:
<223> OTHER INFORMATION: Synthetic DNA

<400> SEQUENCE: 7
gcgggcacat tcctgctgtc atttatcatc taagcgcaaa gagacgtact gtgtaggctg      60
gagctgcttc                                                            70
```

```
<210> SEQ ID NO 8
<211> LENGTH: 70
<212> TYPE: DNA
<213> ORGANISM: Artificial
<220> FEATURE:
<223> OTHER INFORMATION: Synthetic DNA

<400> SEQUENCE: 8
gcagcatcgc tcacccaggg aaaggattgc gatgctgcgt tgaaacgtta atgggaatta      60
gccatggtcc                                                            70
```